(12) United States Patent
Dong (10) Patent No.: US 10,441,296 B2
(45) Date of Patent: Oct. 15, 2019

(54) CORER AND METHOD USING SAME

(71) Applicant: Xieping Dong, Jiangxi (CN)

(72) Inventor: Xieping Dong, Jiangxi (CN)

( * ) Notice: Subject to any disclaimer, the term of this patent is extended or adjusted under 35 U.S.C. 154(b) by 0 days.

(21) Appl. No.: 16/258,661

(22) Filed: Jan. 27, 2019

(65) Prior Publication Data

US 2019/0167276 A1     Jun. 6, 2019

Related U.S. Application Data

(63) Continuation of application No. PCT/CN2017/098039, filed on Aug. 18, 2017.

(30) Foreign Application Priority Data

Aug. 19, 2016  (CN) .......................... 2016 1 0689890

(51) Int. Cl.
*A61B 17/16* (2006.01)
*A61F 2/46* (2006.01)

(52) U.S. Cl.
CPC ...... *A61B 17/1637* (2013.01); *A61B 17/1633* (2013.01); *A61F 2/4601* (2013.01); *A61B 17/1635* (2013.01)

(58) Field of Classification Search
CPC . A61B 17/1637; A61B 17/1633; A61B 17/16; A61B 10/02; A61B 17/1635; A61B 17/32053; A61B 10/025; A61B 17/0266; A61B 10/0275; A61F 2/4601
See application file for complete search history.

(56) References Cited

U.S. PATENT DOCUMENTS

| 4,059,115 A | 11/1977 | Jumashev |
| 6,017,348 A | 1/2000 | Hart et al. |
| 2002/0042624 A1 | 4/2002 | Johanson |

FOREIGN PATENT DOCUMENTS

| CN | 2169383 A | 6/1994 |
| CN | 1314793 A | 9/2001 |
| CN | 1585622 A | 2/2005 |
| CN | 201036560 Y | 3/2008 |
| CN | 102118990 A | 7/2011 |
| CN | 105361982 A | 3/2016 |
| CN | 105395236 A | 3/2016 |
| CN | 106037877 A | 10/2016 |
| CN | 206151530 U | 5/2017 |
| GB | 2483089 A | 2/2012 |
| WO | 2011135070 A2 | 11/2011 |
| WO | 2013154230 A1 | 10/2013 |

*Primary Examiner* — Katherine M Shi
*Assistant Examiner* — Michael G Mendoza
(74) *Attorney, Agent, or Firm* — Wayne & Ken, LLC; Tony Hom (57) ABSTRACT

Disclosed are a corer and a method using same. The corer includes a connecting sleeve, a power lever connected to the connecting sleeve, a hook cylinder having an upper end inserted into the connecting sleeve, and a cutting hook connected to a side of the hook cylinder. A full-length opening is vertically formed on a side wall of the hook cylinder. The upper end of the hook cylinder is detachably connected to the connecting sleeve. An arc slot perpendicular to the full-length opening is provided on a side of a lower end of the hook cylinder. The corer solves the problem that the existing corer is unable to extract an intact core because it is unable to transect a core base during non-penetrating coring.

6 Claims, 9 Drawing Sheets

CORER AND METHOD USING SAME

CROSS-REFERENCE TO RELATED APPLICATIONS

This application is a continuation of International Patent Application No. PCT/CN2017/098039, filed on Aug. 18, 2017 which claims the benefit of priority from Chinese Application No. 20160689890.0, filed on Aug. 19, 2016. The contents of the aforementioned applications, including any intervening amendments thereto, are incorporated herein by reference.

TECHNICAL FIELD

The present invention relates to the fields of machinery, architecture, geology, scientific research, material processing and medical equipment, etc., more particularly to a corer and a method using the same.

BACKGROUND OF THE INVENTION

In clinical practice, trephines are often used to cut out a cancellous bone for transplantation or a pathological specimen. However, the trephines usually fail to extract a core, or break the core into several sections because it is unable to transect a core base during extraction. Even a trephine with shallow threads on its inner wall is unable to obtain an intact core, thereby affecting the quality of the obtained core. In addition, intact cores are generally required in the applications such as manufacture, life and exploration; however, a traditional trephine can only cut off the core periphery instead of the core base.

SUMMARY OF THE INVENTION

There exists a problem that the corer hardly extract an intact core because it is unable to transect a core base in a non-penetrating coring process, especially in the medical field.

In order to solve the above problem, the present invention provides a corer and a method using the same.

A corer includes a connecting sleeve, a power lever connected to the connecting sleeve, a hook cylinder having an upper end inserted into the connecting sleeve, and a cutting hook connected to a side of the hook cylinder. A full-length opening is vertically formed on a side wall of the hook cylinder. An upper end of the hook cylinder is detachably connected to the connecting sleeve. An arc slot perpendicular to the full-length opening is provided on a side of a lower end of the hook cylinder. Teeth are arranged on a lower end surface of the hook cylinder along a circumferential direction.

In an embodiment, adjacent teeth on the hook cylinder are in a staggered arrangement.

In an embodiment, the teeth on the hook cylinder are inclined into a ratchet shape in the same direction.

In an embodiment, the upper end of the hook cylinder is inserted into a lower portion of the connecting sleeve and fastened through a fastener; and a plurality of through holes spaced apart are arranged on an upper opening of the hook cylinder along a circumferential direction and penetrate through the fastener.

In an embodiment, the cutting hook includes a handle clamped in the connecting sleeve, a connecting rod passing through the connecting sleeve and the full-length opening in the side wall of the hook cylinder, and a tip clamped in the arc slot on the lower end of the hook cylinder; a tip body of the tip is an arc; an end portion of the tip is a barb-shaped cutting edge; and a bending radian of the tip body is consistent with the radian of the arc slot.

In an embodiment, tangent at a joint between the tip body of the tip of the cutting hook and the connecting rod is perpendicular to the handle.

In an embodiment, a cross section of the hook cylinder is an arc surface fitted with a circular cross section of the connecting rod of the cutting hook; a radian of the cross section of the hook cylinder is consistent with a radian of arc of an outer wall of the connecting rod of the cutting hook.

In an embodiment, the connecting sleeve is a funnel-shaped cylinder which includes a cylindrical upper portion, a conical connecting portion and a cylindrical lower portion.

In an embodiment, a pair of bolt holes is symmetrically provided on a side wall of the upper portion of the connecting sleeve; and a plurality of bolts for rotating the connecting sleeve are arranged in the bolt holes.

In an embodiment, a set of clamping slots are provided on an inner side surface, corresponding to an opening of the hook cylinder, of an inner portion of the connecting sleeve; the clamping slots are configured to clamp the handle of the cutting hook; and an included angle between the clamping slots is 10-25 degrees.

In an embodiment, when the handle is clamped in a first clamping slot, the tip is hidden in the arc slot on the lower end of the hook cylinder; when the handle is clamped in a second clamping slot, the tip is pivoted into the hook cylinder about the connecting rod; and accordingly, when the handle is clamped in a last clamping slot, the tip is rotated to an axis of the hook cylinder.

In an embodiment, the connecting sleeve is connected with the hook cylinder through the fastener; a plurality of connecting holes spaced apart are horizontally arranged on the lower portion of the connecting sleeve along a circumferential direction and penetrate through the fastener. A through slot passing through the cutting hook is vertically provided on the side wall of the lower portion, corresponding to the opening of the hook cylinder. An annular slot is provided at a lower opening of the lower portion along a circumferential direction; the hook cylinder is inserted into the annular slot; and a width of the annular slot is adapted to a wall thickness of the hook cylinder.

In an embodiment, an inner upper wall of the lower portion of the connecting sleeve is in a threaded connection with a power lever; and the power lever is driven by a motor or other work-saving devices.

A use method of the corer includes:

step 1, clamping the handle of the cutting hook into a first clamping slot in the connecting sleeve to hide the tip in an arc slot;

step 2, manually driving a hook cylinder, or with a motor or other work-saving devices by connecting a power lever to cut a core to a desired depth;

step 3, rotating the cutting hook to clamp the handle into a second clamping slot;

step 4, reversely rotating the corer for one circle to annularly cut a shallow layer of a core base;

step 5, repeating steps 3 and 4 to cut a deeper layer of the core base till the handle of the cutting hook is clamped in the last clamping slot in the connecting sleeve, and then reversely rotating the corer for one circle to cut off the core base;

step 6, keeping the handle clamped in the last clamping slot to allow the tip to support the core base, and removing the corer; and step 7, clamping the handle in the first clamping slot to hide the tip in the arc slot of the hook cylinder, removing the fastener used for fixing the connecting sleeve and the hook cylinder, and pushing out the core using a rod with an inner diameter slightly smaller than that of the hook cylinder.

In an embodiment, the first clamping slot in step 1 is the clamping slot in the connecting sleeve, corresponding to the handle, when the tip is hidden in the arc slot of the hook cylinder.

In an embodiment, the last clamping slot in step 5 is the clamping slot on the connecting sleeve, corresponding to the handle, when the tip is rotated to the axis of the hook cylinder.

In an embodiment, the reverse direction in steps 4 and 5 is opposite to the position of the clamping slot, that is, the corer is rotated anticlockwise if the clamping slot and the tip are correspondingly positioned in a clockwise direction of the handle, so that the tip annularly cuts the core base in a way of hooking instead of pressing, so as to reduce a cutting resistance to make the cutting smooth and reduce faults and part loss. Vice versa, the corer is rotated clockwise if the clamping slot and the tip are correspondingly positioned in an anticlockwise direction of the handle.

As compared to the prior art, for example in the medical field, the present invention overcomes the defect that the traditional device for cutting off a bone is unable to extract an intact bone core because it is unable to transect a bone core base. In the present invention, the tip of the cutting hook transects the bone core base before the bone core is extracted, so that an intact bone core can be obtained. The tip also supports the bone core during the coring to help the extraction of the bone core. The cutting hook can transect the bone core base by clamping the handle into a set of clamping slots on the connecting sleeve in sequence and rotating the hook cylinder, which is easy to operate and convenient to use. The staggered teeth on the lower end surface of the hook cylinder improve the sawing efficiency of the hook cylinder.

The present invention is used to cut off cores of objects or for the manufacture of cylindrical objects, which can be widely used in the applications such as machinery, architecture, geology, scientific research, material processing and medical equipment.

BRIEF DESCRIPTION OF THE DRAWINGS

The present invention is further described below in detail in conjunction with accompanying drawings.

In the drawings: 1: hook cylinder; 11: opening; 12: arc slot; 13: tooth; 14: through hole; 2: connecting sleeve; 21: upper portion; 211: clamping slot; 212: bolt hole; 213: bolt; 22: connecting portion; 23: lower portion; 231: connecting hole; 232: through slot; 233: annular slot; 234: threaded through hole; 3: cutting hook; 31: connecting rod; 32: handle; 33: tip; 331: tip body; 332: cutting edge; 4: power lever; and 5: fastener.

DETAILED DESCRIPTION OF EMBODIMENTS

Figure 1:
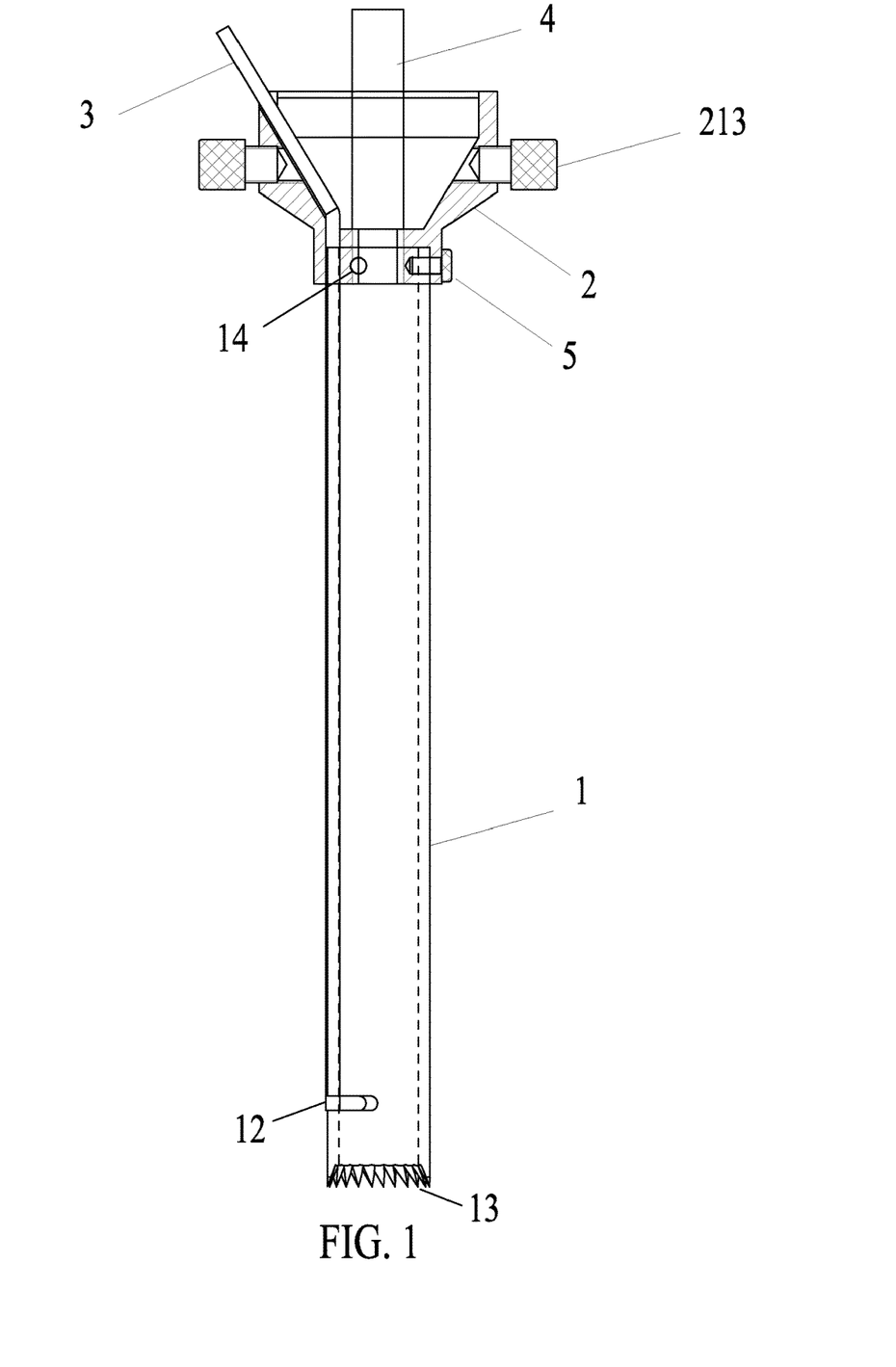
FIG. 1 is a front view of a corer of the present invention.
Figure 2:
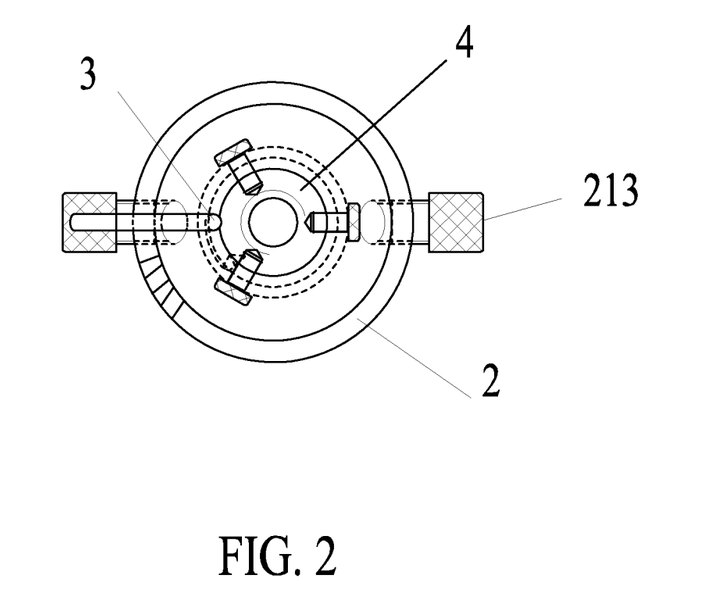
FIG. 2 is a top view of the corer of the present invention.

As shown in FIGS. 1 and 2, this embodiment illustrates a corer, including a connecting sleeve 2, a power lever 4 connected to the connecting sleeve, a hook cylinder 1 having an upper end inserted into the connecting sleeve 2, and a cutting hook 3 connected to a side of the hook cylinder 1. A full-length opening 11 is vertically formed on a side wall of the hook cylinder 1. An upper end of the hook cylinder 1 is detachably connected to the connecting sleeve 2. An arc slot 12 perpendicular to the full-length opening 11 is provided on a side of a lower end of the hook cylinder 1.

Figure 8:
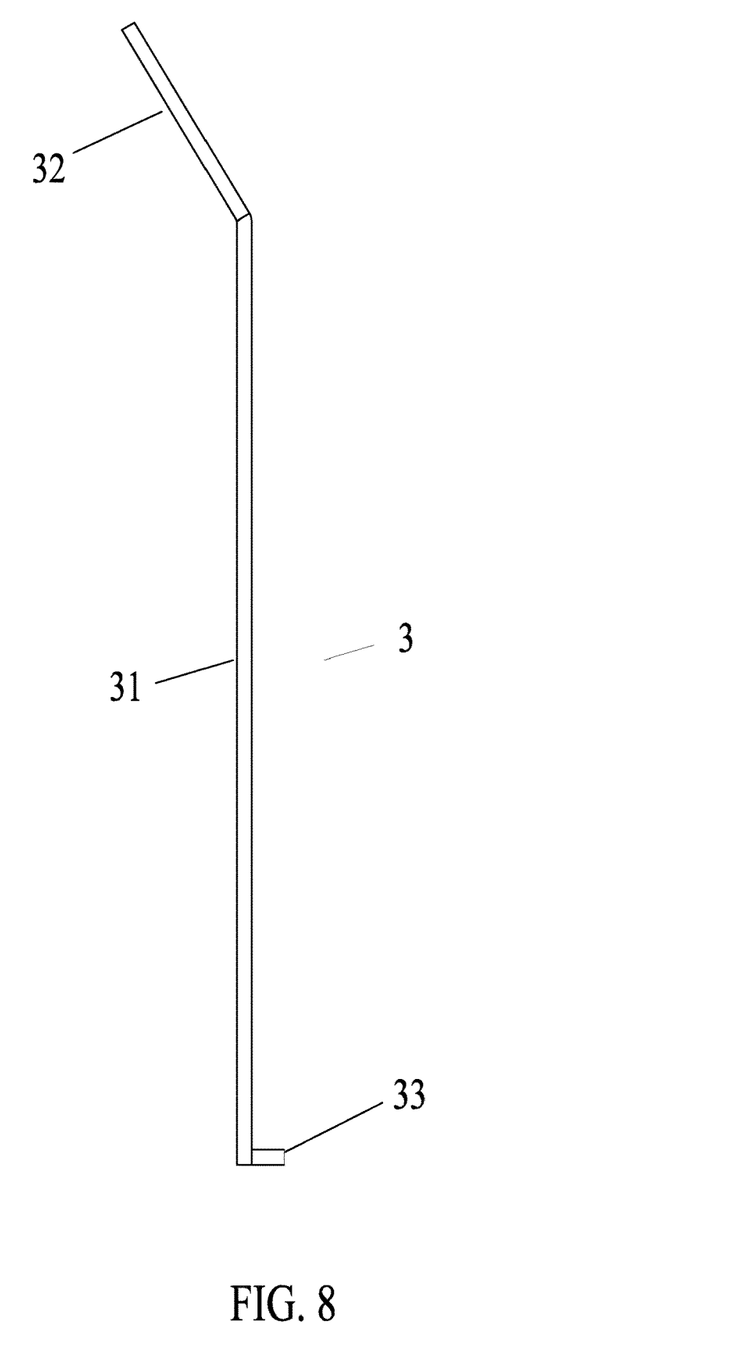
FIG. 8 is a front view of a cutting hook.
Figure 9:
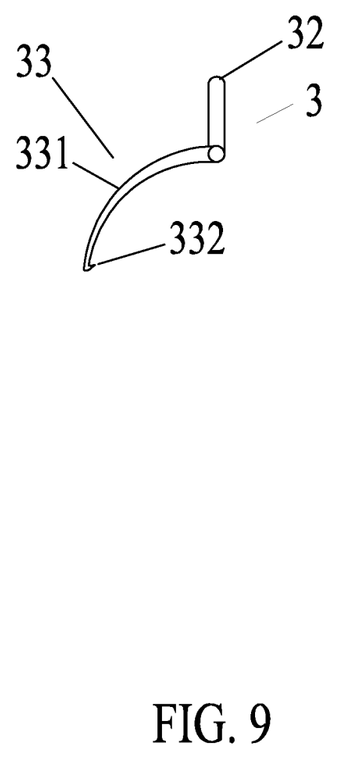
FIG. 9 is a top view of the cutting hook.

As shown in FIGS. 8 and 9, the cutting hook 3 includes a handle 32 clamped in the connecting sleeve 2, a connecting rod 31 passing through the connecting sleeve 2 and the full-length opening on the side wall of the hook cylinder 1, and a tip 33 clamped in the arc slot 12 at the lower end of the hook cylinder 1. The handle 32 and the tip 33 are respectively provided on the upper and lower ends of the connecting rod 31. A tip body 331 of the tip 33 is an arc and an end portion of the tip is a barb-shaped cutting edge 332. A bending radian of the tip body 331 is consistent with a radian of the arc slot 12. A maximum width of the tip 33 is consistent with the wall thickness of the hook cylinder 1. When the handle 32 is positioned in a first clamping slot 211, the tip 33 is completely hidden in the arc slot 12. Tangent at a joint between the tip body 331 of the cutting hook 3 and the connecting rod 31 is perpendicular to the handle 32.

Figure 3:
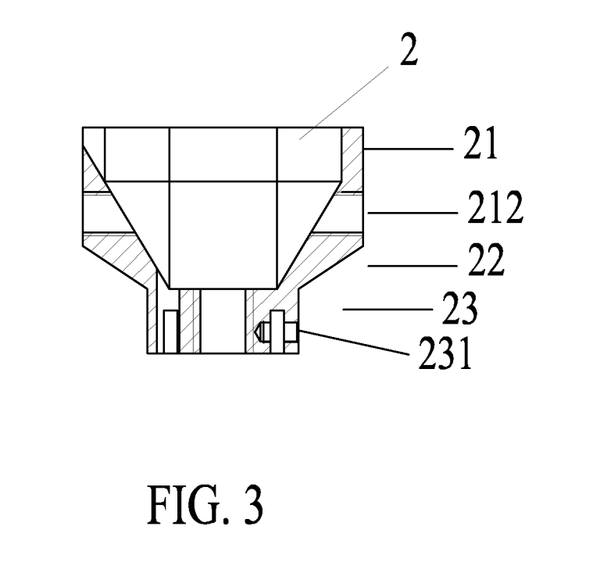
FIG. 3 is a front view of a connecting sleeve.
Figure 4:
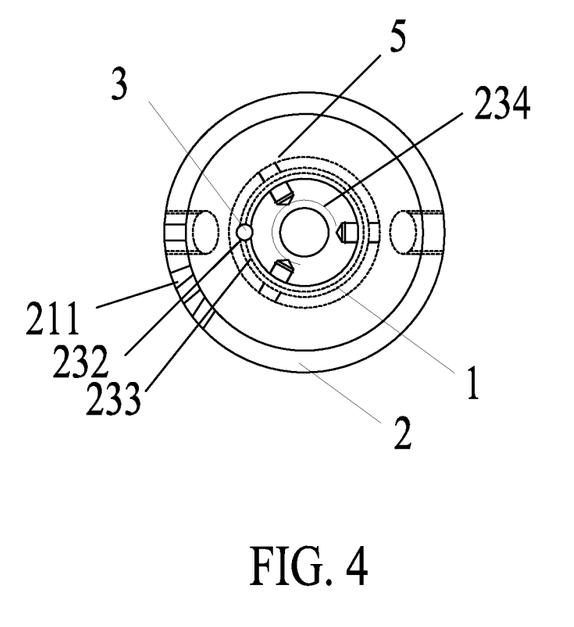
FIG. 4 is a top view of the connecting sleeve.
Figure 10:
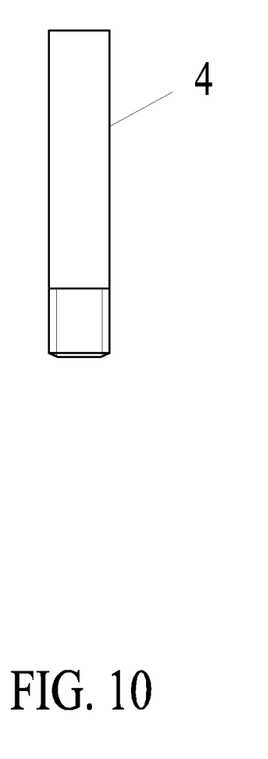
FIG. 10 is a schematic diagram of a power lever.

As shown in FIGS. 3 and 4, the connecting sleeve 2 is a funnel-shaped cylinder which includes a cylindrical upper portion 21, a conical connecting portion 22 and a cylindrical lower portion 23. The handle 32 applies an elastic stress to the inner wall of the connecting sleeve 2 so that the handle 32 is easily clamped into the clamping slot 211. A set of clamping slots 211 for clamping the handle 32 of the cutting hook 3 are provided on an inner side surface, corresponding to an opening 11 of the hook cylinder 1, of an upper portion 21 of the connecting sleeve 2. A first clamping slot 211 is positioned corresponding to the handle 32 on the connecting sleeve 2 when the tip 33 of the cutting hook 3 is completely hidden in the arc slot 12 of the hook cylinder 1. An included angle between the last clamping slot and the first clamping slot is less than 90 degrees. The included angle between the clamping slots 211 should be minimized if the strength of the material of the connecting sleeve 2 is satisfied. When more clamping slots 211 are arranged, the resistance to the cutting of the tip 33 becomes smaller during the rotation of the corer and the cutting is easier. The clamping slots 211 are provided anticlockwise on an opening of the upper portion 21 of the connecting sleeve 2 in the present embodiment, and can also be provided clockwise in other embodiments. Correspondingly, the position of the arc slot 12 on the hook cylinder 1 and the rotating direction of the corer during use are also opposite to the position of clamping slots in the present embodiment. The set of clamping slots includes at least four clamping slots. When the handle 32 is clamped in the first clamping slot 211, the tip 33 of the cutting hook 3 is completely hidden in the arc slot 12 of the hook cylinder 1. When the handle 32 is clamped in the second clamping slot 211, the tip 33 of the cutting hook 3 is pivoted into the hook cylinder 1 about the connecting rod 31 in such an angle that the resistance when the hook cylinder 1 cuts a core base is minimum, avoiding being stuck or damage to the cutting hook 3. An annular incision can be cut out in the core base. When the handle 32 is clamped in the third clamping 211, the tip 33 of the cutting hook 3 is continuously rotated in a small angle into the hook cylinder 1 to cut the core base. When the handle 32 is clamped in the last clamping slot 211, the tip 33 of the cutting hook 3 is continuously rotated into the hook cylinder 1 to the axis of the hook cylinder 1. An included angle between adjacent clamping slots 211 is 10-25 degrees. A pair of bolt holes 212 is symmetrically provided on the side wall of the upper portion 21 of the connecting sleeve 2. A plurality of bolts 213 for rotating the connecting sleeve 2 are arranged in the bolt holes 212. The connecting sleeve 2 is connected to the hook cylinder 1 through a fastener 5. A plurality of connecting holes 231 spaced apart are horizontally arranged on the lower portion 23 of the connecting sleeve 2 along a circumferential direction and pass through the fastener 5. A through slot 232 passing through the cutting hook 3 is vertically provided on the side wall of the lower portion 23, corresponding to the opening of the hook cylinder 1. An annular slot 233 is provided at a lower opening of the lower portion 23 of the connecting sleeve along a circumferential direction. The hook cylinder 1 is inserted into the annular slot 233. The width of the annular slot 233 is adapted to the wall thickness of the hook cylinder 1. A threaded through hole 234 connected with the power lever is further provided in a middle of the lower portion 23 of the connecting sleeve 2. The middle of the lower portion 23 of the connecting sleeve 2 is in a threaded connection with the power lever 4. The power lever is driven by a motor or other work-saving devices. The power lever 4 is a rigid or flexible straight lever. The lower end is a threaded portion connected to the threaded through hole 234 on the lower portion of the connecting sleeve 2.

Figure 5:
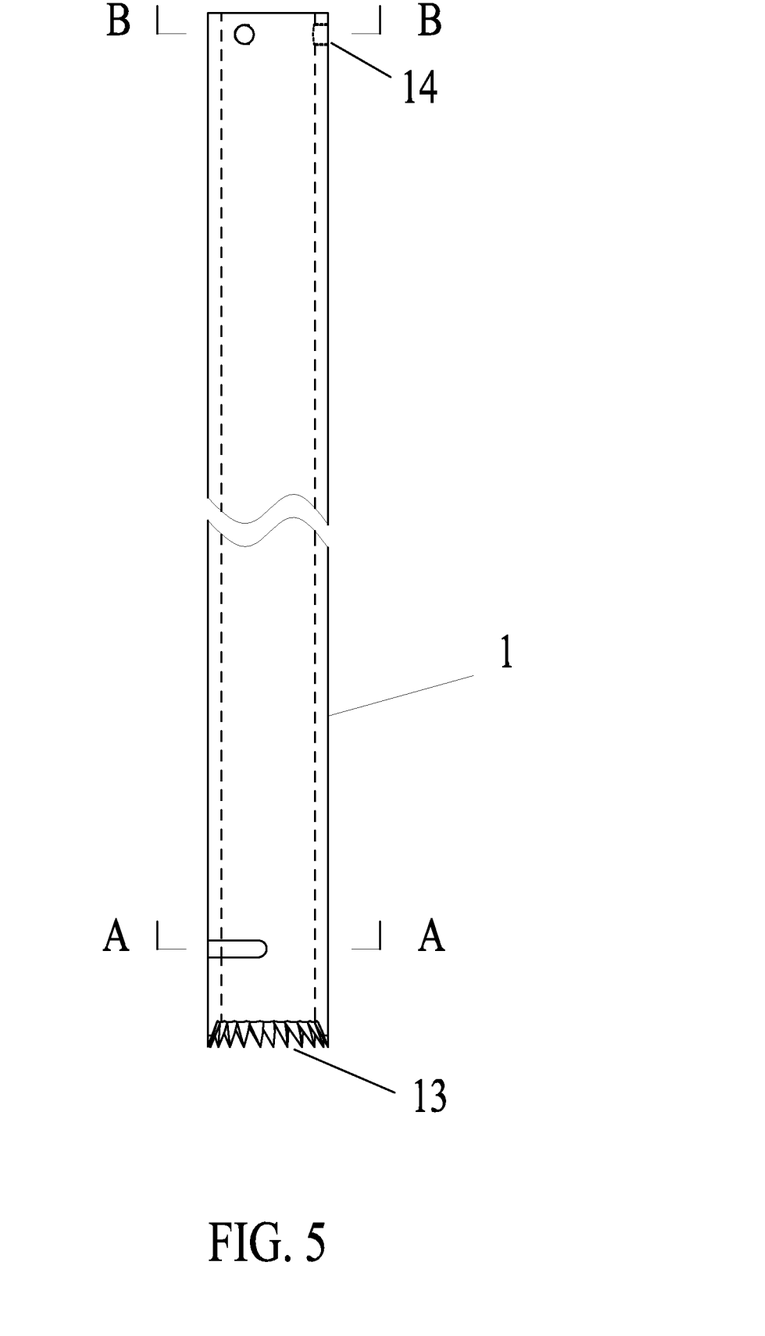
FIG. 5 is a top view of a hook cylinder.
Figure 6:
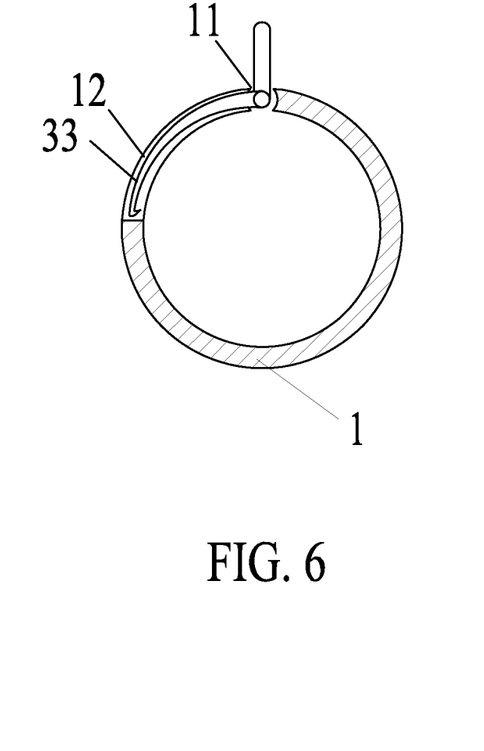
FIG. 6 is a sectional view taken along A-A in FIG. 5.
Figure 7:
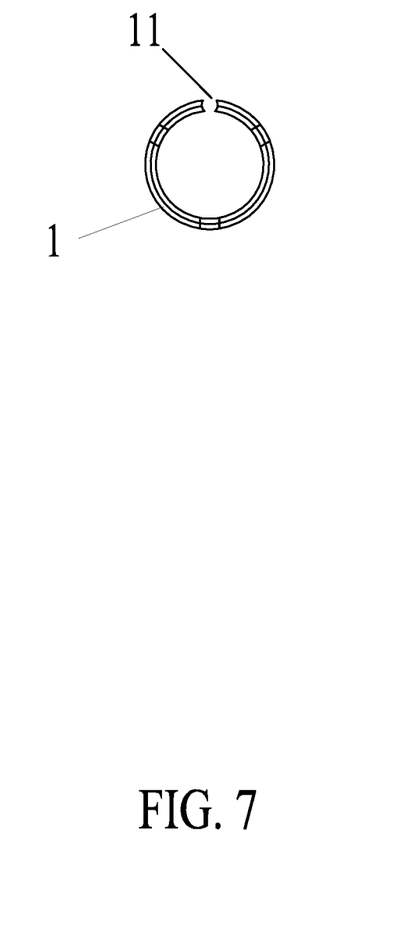
FIG. 7 is a sectional view taken along B-B in FIG. 5.

As shown in FIGS. 5, 6 and 7, a cross section of the hook cylinder 1 at both sides of the opening 11 on the side wall is an arc surface. The cross section of the hook cylinder is fitted with a circular cross section of the connecting rod 31 of the cutting hook 3. A radian of the section of the hook cylinder is consistent with a radian of the arc of the outer wall of the connecting rod 31 of the cutting hook 3, so that the connecting rod 31 may be firmly clamped on the hook cylinder 1 and prevented from being ejected out of the opening on the hook cylinder 1. The upper end of the hook cylinder 1 is inserted into the annular slot 233 of the lower portion 23 of the connecting sleeve 2. A plurality of through holes 14 spaced apart are arranged on the upper opening of the hook cylinder 1 along a circumferential direction and penetrate through the fastener. Teeth 13 are arranged on the lower end surface of the hook cylinder 1 along a circumferential direction. The adjacent teeth 13 are in a staggered arrangement in or are inclined into a ratchet in the same direction.

A method using the corer is described as follows, taking the femoral neck coring as an example.

A patient lies on his back. A longitudinal incision having a length of a few centimeters is cut below the greater trochanter of the lateral femur of the upper thigh to expose the bone cortex. A guide needle is drilled into the center of a femoral head necrotic focus along the femoral neck in close proximity to the base of the greater trochanter. It can be observed from an anteroposterior & lateral view that the guide needle is centered. A hollow drill is threaded into the guide needle to break the bone cortex. Then a corer, with an inner diameter that is equal to the outer diameter of the hollow drill and an outer diameter that is equal to the inner diameter, of a hook cylinder 1 of the corer is threaded into the hollow drill. The handle 32 of a cutting hook 3 is clamped into an first clamping slot 211 on a connecting sleeve 2 to hide a tip 33 in an arc slot 12 of the hook cylinder 1. Next, the hook cylinder 1 of the corer is threaded into a catheter corer. The corer is rotated to cut out an annular channel in the femoral neck. In order to strengthen the power, the upper end of the corer may be connected to the power lever 4 where an electric drill drives the corer to rotate and cut.

After the position of the corer is determined through scales and image monitoring, the cutting hook 3 is rotated anticlockwise to clamp the handle 32 into the second clamping slot 211 and the tip 33 is pivoted into the hook cylinder 1. The connecting sleeve 2 is grasped to rotate the corer clockwise for one circle to cut out an annular incision in the core base. The above-mentioned processes are repeated till the handle 32 of the cutting hook 3 is clamped into the last clamping slot 211 on the connecting sleeve 2, and then the connecting sleeve 2 is grasped to rotate the corer clockwise for one circle to completely cut off the bone core base. At this moment, the tip 33 is positioned in the center of the bone core. The intact bone core can be extracted under the support of the cutting hook 3 after the corer is evacuated. An annular channel is formed in the femoral neck, thereby reducing the pressure on the femoral head and creating a possibility for removal of the femoral head necrotic foci and the bone grafting.

The present invention can be used to obtain cores in the medical field or cut out cylindrical objects in the fields of machinery and architecture, for example, the corer of the present invention can be used to cut off latex, rubber, concrete and similar core materials.

When the handle 32 is clamped in the first clamping slot 211, the tip 33 is hidden in the arc slot 12 on the lower end of the hook cylinder 1. When the handle 32 is clamped in the second clamping slot 211, the tip 33 is pivoted into the hook cylinder 1 about the connecting rod 31. Accordingly, the tip 33 is pivoted to the axis of the hook cylinder 1 when the handle 32 is clamped in the last clamping slot 211.

Before the corer is shipped out of a factory, the full-length opening 11 is formed on the side wall of the hook cylinder 1; a gap is formed in the teeth 13 at the lower end of the hook cylinder 1. In order to fill the gap, it is required to seal part of the opening on the side wall of the hook cylinder 1 below the arc slot 12 using teeth fragments after the cutting hook is assembled, so as to guarantee an intact ring structure formed by teeth.

The method using the corer is basically the same with the above embodiment, including:

step 1, clamping a handle 32 of a cutting hook 3 into a first clamping slot 211 in a connecting sleeve 2 to hide a tip 33 in an arc slot 12;

step 2, manually driving a hook cylinder 1, or driving a hook cylinder 1 with a motor or other work-saving devices by connecting a power lever 4 to cut a core to a required depth;

step 3, rotating the cutting hook 3 to clamp the handle 32 into a second clamping slot 211;

step 4, reversely rotating the corer for one circle to annularly cut a shallow layer of a core base;

step 5, repeating steps 3 and 4 to cut a deeper layer of the core base till the handle 32 of the cutting hook 3 is clamped in a last clamping slot 211 on the connecting sleeve 2, and then reversely rotating the corer for one circle to cut off the core base;

step 6, maintaining the handle 32 clamped in the last clamping slot 211 to allow the tip 33 to support the core base, and taking out the corer; and step 7, clamping the handle 32 in the first clamping slot 211 to hide the tip 33 in the arc slot 12 of the hook cylinder 1 again, removing a fastener 5 which is used for fixing the connecting sleeve 2 and the hook cylinder 1, and pushing out a core by using a rod having an inner diameter slightly less than that of the hook cylinder 1 to end the use.

The reverse direction in steps 4 and 5 is opposite to the position of the clamping slot 211. That is, the corer is rotated anticlockwise if the clamping slot 211 and the tip 33 are correspondingly positioned in a clockwise direction of the handle 32, so that the tip 33 annularly cuts the core base in a way of hooking instead of pressing, so as to reduce a cutting resistance to make the cutting smooth and reduce faults and part loss. Vice versa, the corer is rotated clockwise if the clamping slot 211 and the tip 33 are correspondingly positioned in an anticlockwise direction of the handle 32.

What is claimed is:

1. A corer, comprising:
   a connecting sleeve;
   a power lever connected to the connecting sleeve;
   a hook cylinder having an upper end inserted into the connecting sleeve; and
   a cutting hook connected to a side of the hook cylinder;
   wherein a full-length opening is vertically formed on a side wall of the hook cylinder; an upper end of the hook cylinder is detachably connected to the connecting sleeve, and an arc slot perpendicular to the full-length opening is provided on a side of a lower end of the hook cylinder; and a plurality of teeth are arranged on a lower end surface of the hook cylinder along a circumferential direction;
   a cross section of the hook cylinder at both sides of the opening on the side wall is an arc surface; the cross section of the hook cylinder is fitted with a circular cross section of a connecting rod of the cutting hook; a radian of the cross section of the hook cylinder is consistent with a radian of an arc of an outer wall of the connecting rod of the cutting hook;
   the connecting sleeve is a funnel-shaped cylinder which comprises a cylindrical upper portion, a conical connecting portion and a cylindrical lower portion;
   a set of clamping slots are provided on an inner side surface, corresponding to an opening of the hook cylinder, of an upper portion of the connecting sleeve; the clamping slots are configured to clamp a handle of the cutting hook; an included angle between the clamping slots is 10-25 degrees; and
   a pair of bolt holes is symmetrically provided on a side wall of the upper portion of the connecting sleeve; a plurality of bolts for rotating the connecting sleeve are arranged in the bolt holes.

2. The corer of claim 1, wherein adjacent teeth on the hook cylinder are staggered.

3. The corer of claim 1, wherein the upper end of the hook cylinder is inserted into a lower portion of the connecting sleeve and fastened through a fastener; and a plurality of through holes spaced apart are arranged on an upper opening of the hook cylinder along a circumferential direction and penetrate through the fastener.

4. The corer of claim 1, wherein the cutting hook comprises:
   the handle clamped in the connecting sleeve;
   the connecting rod passing through the connecting sleeve and the full-length opening on the side wall of the hook cylinder; and
   a tip clamped in the arc slot on the lower end of the hook cylinder;
   a tip body of the tip is an arc; an end portion of the tip is a barb-shaped cutting edge; a bending radian of the tip body is consistent with the radian of the arc slot.

5. The corer of claim 4, wherein tangent of a joint between the tip body of the cutting hook and the connecting rod is perpendicular to the handle.

6. The corer of claim 1, wherein a plurality of connecting holes spaced apart are horizontally arranged on a lower portion of the connecting sleeve along a circumferential direction and penetrate through a fastener;
   a through slot passing through the cutting hook is vertically provided on the side wall of the lower portion, corresponding to the opening of the hook cylinder;
   an annular slot is provided at a lower opening of the lower portion of the connecting sleeve along a circumferential direction; the hook cylinder is inserted into the annular slot; a width of the annular slot is adapted to a wall thickness of the hook cylinder; and
   a middle of the lower portion of the connecting sleeve is in a threaded connection with a power lever.

* * * * *